(12) United States Patent
Hübsch

(10) Patent No.: US 6,251,574 B1
(45) Date of Patent: Jun. 26, 2001

(54) COLOR PHOTOGRAPHIC DEVELOPER CONCENTRATE

(75) Inventor: Thomas Hübsch, Köln (DE)

(73) Assignee: Agfa-Gevaert (BE)

( * ) Notice: Subject to any disclaimer, the term of this patent is extended or adjusted under 35 U.S.C. 154(b) by 0 days.

(21) Appl. No.: 09/593,430

(22) Filed: Jun. 14, 2000

(30) Foreign Application Priority Data

Jun. 17, 1999 (DE) .............................................. 199 27 602

(51) Int. Cl.$^7$ .................................................. G03C 7/413
(52) U.S. Cl. .......................................... 430/466; 430/490
(58) Field of Search ..................................... 430/466, 490

(56) References Cited

U.S. PATENT DOCUMENTS 5,891,609 * 4/1999 Papai ..................................... 430/466

OTHER PUBLICATIONS

Patent application Serial No. 09/545,376 filed on Apr. 7, 2000.*

* cited by examiner

*Primary Examiner*—Hoa Van Le
(74) *Attorney, Agent, or Firm*—Connolly Bove Lodge & Hutz LLP

(57) ABSTRACT

A one-part, multi-phase colour developer concentrate having an aqueous phase and an organic phase, wherein the organic phase is constituted by a carboxylic acid amide or urea derivative which is liquid at room temperature and the concentrate contains at least one compound of the formulae (I), (II) or (III) as antioxidant:

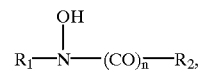

(I)

in which $R_1$ means alkyl, $R_2$ means alkyl or aryl and n means 0 or 1 and at least one of the residues $R_1$ and $R_2$ contains at least one —OH, —COOH or —SO$_3$H group;

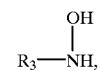

(II)

in which $R_3$ means an alkyl or acyl group;

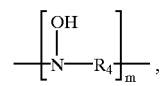

(III)

in which $R_4$ means an alkylene group optionally interrupted by O atoms and m means a number of at least 2, is in particular suitable for the production of a colour developer solution for silver halide materials having an elevated AgCl content.

8 Claims, No Drawings

COLOR PHOTOGRAPHIC DEVELOPER CONCENTRATE

The developer solution for developing colour photographic materials, in particular for developing colour photographic paper, is prepared from or, in the case of continuous operation, replenished with concentrates which contain the necessary constituents.

It is conventional to provide three different concentrates, as certain constituents of the developer bath are not mutually compatible on extended storage. Thus, for example, one concentrate contains the antioxidant, an auxiliary solvent and an optical brightener, a second concentrate contains the colour developer substance, for example CD 3 (4-N-ethyl-4-N-(2-methylsulfonylaminoethyl)-2-methyl-p-phenylenediamine) and a third concentrate contains the buffer substance, alkali and a water softener.

There has been no lack of attempts to develop stable, one-part colour developer concentrates as handling errors during preparation or replenishing of a developer solution may consequently be avoided.

Two one-part, multi-phase concentrates are currently commercially available, a) Monolineg® RA-4 CD-R from Tetenal, a two-phase concentrate with an elevated solids content and b) TriPhase® RA-4 CD-R from Trebla, a three-phase concentrate with undissolved constituents in the middle phase (c.f. also U.S. Pat. No. 5,891,609).

A characteristic feature of the one-part, multi-phase colour developer concentrate according to U.S. Pat. No. 5,891,609 is the use of a monoheterocyclic amide as solvent for the colour developer substance and the use of an inorganic antioxidant, in particular a sulfite. Diethylhydroxylamine is additionally used as antioxidant.

The colour developer substance, like the diethylhydroxylamine, is substantially present in the organic phase, while the sulfite is in the aqueous-alkaline phase.

Using relatively large quantities of sulfite in developers for colour photographic materials, the silver halide emulsions of which substantially consist of AgCl, as is conventional in colour photographic paper, is disadvantageous as sulfite has an inhibiting effect on development in such materials, such that satisfactory colour densities are not achieved, especially in rapid processing systems (development times of less than 45 seconds).

Diethylhydroxylamine is disadvantageous due to its unpleasant odour.

Since development is increasingly performed in decentralised apparatus, or "minilabs", which are frequently installed in department stores or chemist's shops and provide "one-hour" processing, such an odour nuisance is unacceptable.

The object of the invention was accordingly to provide a one-part colour developer concentrate which largely, if not entirely, dispenses with diethylhydroxylamine as antioxidant, but is nevertheless stable on exposure to atmospheric oxygen and provides unimpaired sensitometric results, even with short development times.

This object is achieved by the organic, water-soluble hydroxylamine derivatives listed below. This is surprising because these compounds largely accumulate in the aqueous phase and the organic phase containing the colour developer accordingly contains no or virtually no antioxidant.

The present invention accordingly provides a one-part, multi-phase colour developer concentrate having an aqueous phase and an organic phase, wherein the organic phase is constituted by one or more partially water-miscible solvents and the concentrate contains at least one compound of the formulae (I), (II) or (III) as antioxidant:

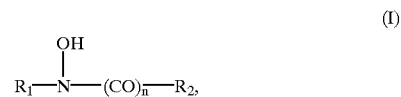
(I)

in which $R_1$ means alkyl, $R_2$ means alkyl or aryl and n means 0 or 1 and at least one of the residues $R_1$ and $R_2$ contains at least one —OH, —COOH or —$SO_3H$ group;

(II)

in which $R_3$ means an alkyl or acyl group;

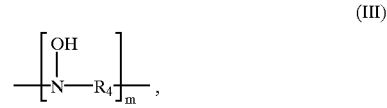
(III)

in which $R_4$ means an alkylene group optionally interrupted by O atoms and m means a number of at least 2.

The alkyl groups $R_1$, $R_2$, $R_3$, the alkylene group $R_4$ and the aryl group $R_2$ may bear further substituents in addition to the stated substitution.

Examples of suitable antioxidants are

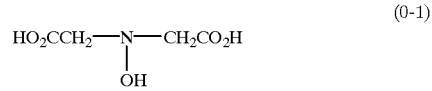
(0-1)

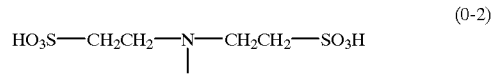
(0-2)

(0-3)

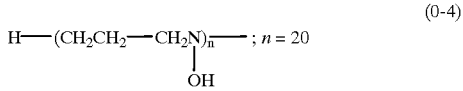
(0-4)

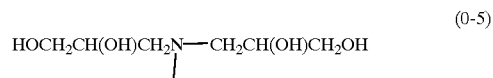
(0-5)

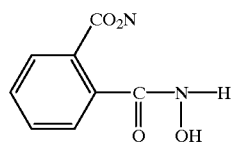
(0-6)

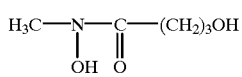
(0-7)

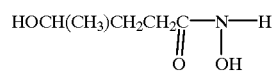
(0-8)

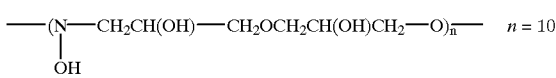 $n = 10$
(0-9)

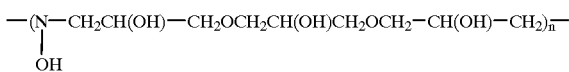
(0-10)

$n = 5$

Compounds 0–2, 0–7 and 0–10 are preferred.

The antioxidants are preferably used in a quantity of 0.1 to 5 mol/l of concentrate or, as far as oligomeric and polymeric compounds are concerned, in a quantity of from 10 to 500 g/l of concentrate.

Suitable organic solvents are carboxylic acid amide and urea derivatives, for example dimethylfonnamide, methylacetamide, dimethylacetamide, N,N'-dimethylurea, tetramethylurea, methanesulfonamide, dimethylethyleneurea, N-acetylglycine, N-valeramide, isovaleramide, N-butyramide, N,N-dimethylbutyramide, N-(2-hydroxyphenyl)acetamide, N-(2-methoxyphenyl) acetamide, 2-pyrrolidinone, ε-caprolactam, acetanilide, benzamide, toluenesulfonamide, phthalimide;

aliphatic and cyclic alcohols, for example isopropanol, tert.-butyl alcohol, cyclohexanol, hydroxylmethylcyclohexane, bis(hydroxymethyl) cyclohexane;
  aliphatic and cyclic polyalcohols, for example glycols, polyglycols, polywaxes, trimethyl-1,6-hexanediol, glycerol, 1,1,1-trimethylolpropane, pentaerythritol, sorbitol;
  aliphatic and cyclic ketones, for example acetone, ethyl methyl ketone, diethyl ketone, tert.-butyl methyl ketone, diisobutyl ketone, acetylacetone, acetonylacetone, cyclopentanone, acetophenol;
  aliphatic and cyclic carboxylic acid esters and orthoesters, for example trimethoxymethane, methyl acetate, allyl acetate, ethylene glycol monomethyl ether acetate, ethylene glycol diacetate, glycerol 1-acetate, glycerol diacetate, methylcyclohexyl acetate, methyl salicylate, phenyl salicylate;
  aliphatic and cyclic phosphonic acid esters, for example methylphosphonic acid dimethyl ester, allylphosphonic acid diethyl ester;
  aliphatic and cyclic oxoalcohols, for example 4-hydroxy-4-methyl-2-pentanone, salicylaldehyde;
  aliphatic and cyclic aldehydes, for example acetaldehyde, propanal, trimethylacetaldehyde, crotonaldehyde, glutaraldehyde, 1,2,5,6-tetrahydrobenzaldehyde, benzaldehyde, terephthalaldehyde;
  aliphatic and cyclic oximes, for example butanone oxime, cyclohexanone oxime;
  aliphatic and cyclic amines (primary, secondary or tertiary), for example ethylamine, diethylamine, triethylamine, dipropylamine, pyrrolidine, morpholine, 2-aminopyrimidine;
  aliphatic and cyclic polyamines (primary, secondary or tertiary), for example ethylenediamine, 1-amino-2-diethylaminoethane, methyl-bis-(2-methylaminoethyl) amine, permethyldiethylenetriamine, 1,4-cyclohexanediamine, 1,4-benzenediamine;
  aliphatic and cyclic hydroxyamines, for example ethanolamine, 2-methylethylamine, 2-methylaminoethanol, 2-(dimethylamino)ethanol, 2-(2-dimethylaminoethoxy)ethanol, diethanolamine, N-methyldiethanolamine, triethanolamine, 2-(2-aminoethylamino)ethanol, trilsopropanolamine, 2-amino-2-hydroxymethyl-1,3-propanediol, 1-piperidineethanol, 2-aminophenol, barbituric acid, 2-(4-aminophenoxy)ethanol, 5-amino-1-naphthol.

Good phase separation is achieved using the stated solvents individually and as mixtures.

Caprolactam, polyglycols, glycols, dimethylacetamide and triethanolamine are preferred solvents.

Processing conditions, suitable colour developer substances, suitable buffer substances, suitable water softeners, suitable optical brighteners, auxiliary developers, wetting agents, development accelerators and antifogging agents are described on pages 102 to 107 of Research Disclosure 37 038 (February 1995). Many advantageously used substances are stated on pages 12 to 25 of EP 686 875.

CD-3 is the preferred colour developer substance.

EXAMPLE 1

Two multi-phase, one-part developer concentrates are prepared, wherein concentrate 1-1 was produced according to Example 1 of U.S. Pat. No. 5,891,609 and is of the following composition:

| | |
|---|---|
| Potassium sulfite | 4 g |
| CD 3 | 70 g |
| Caprolactam | 120 g |
| Optical brightener | 10 g |
| Potassium carbonate | 240 g |
| Polymaleic acid, 50 wt. % aqueous solution | 30 ml |
| Na$_5$DTPA, 40 wt. % aqueous solution | 20 ml |
| Diethylhydroxylamine, 85 wt. % aqueous solution | 70 ml |
| Wetting agent solution | 8 ml |

1-2 contains compound 0-2 as antioxidant and is of the following composition:

| | |
|---|---|
| Antioxidant 0-2 | 39 g |
| CD 3 | 70 g |
| Hydroxylamine | 1.25 g |
| ε-Caprolactam | 100 g |
| Diethylene glycol | 80 ml |
| Optical brightener | 10 g |
| EDTA | 30 g |
| Polymaleic acid solution | 30 ml |

-continued

| | |
|---|---|
| Potassium carbonate | 145 g |
| Sodium carbonate | 15 g |
| Na$_5$DTPA, 40 wt. % aqueous solution | 20 ml |
| Sodium hydroxide | 20 g |
| make up to 1 liter with water. | |

The concentrates are stored for two weeks at 60° C. and the CD 3 content thereof is then tested. Of the original quantity, 97% is still present in concentrate 1-1 and 97% is still present in concentrate 1-2.

The concentrates dissolve in 9 l of water to produce a ready-to-use developer in 4.5 minutes in the case of 1-1 and in only 30 seconds in the case of 1-2.

EXAMPLE 2

A colour photographic recording material was produced by applying the following layers in the stated sequence onto a layer support of paper coated on both sides with polyethylene. Quantities are stated in each case per 1 m². The silver halide application rate is stated as the corresponding quantities of AgNO$_3$.

Layer Structure 1

1st Layer (substrate layer):

0.3 g of gelatine

2nd Layer (blue-sensitive layer):

Blue-sensitive silver halide emulsion (99.5 mol % AgCl, 0.5 mol % AgBr, average grain diameter 0.9 μm) prepared from 0.635 g of gelatine 0.35 g of yellow coupler GB-1

0.15 g of yellow coupler GB-2

0.38 g of tricresyl phosphate (TCP)

3rd Layer (interlayer)

1.1 g of gelatine 0.08 g of scavenger SC 0.02 of white coupler WK 0.1 g of TCP

4th Layer (green-sensitive layer):

Green-sensitive silver halide emulsion (99.5 mol % AgCl, 0.5 mol % AgBr, average grain diameter 0.47 μm) prepared from 0.23 g of AgNO$_3$ 1.2 g of gelatine 0.23 g of magenta coupler PP-1

0.23 g of colour stabiliser ST-1

0.17 g of colour stabiliser ST-2

0.23 g of TCP

5th Layer (UV protective layer):

1.1 g of gelatine 0.08 g of SC 0.02 g of WK 0.6 g of UV absorber UV 0.1 g of TCP 6th Layer (red-sensitive layer):

Red-sensitive silver halide emulsion (99.5 mol % AgCl, 0.5 mol % AgBr, average grain diameter 0.5 μm) prepared from 0.26 g of AgNO$_3$ with 0.75 g of gelatine 0.40 g of cyan coupler BG-1

0.36 g of TCP

7th Layer (UV protective layer):

0.35 g of gelatine 0.15 g of UV 0.075 g of TCP

8th Layer (protective layer):

0.9 g of gelatine 0.3 g of hardener HM

GB-1

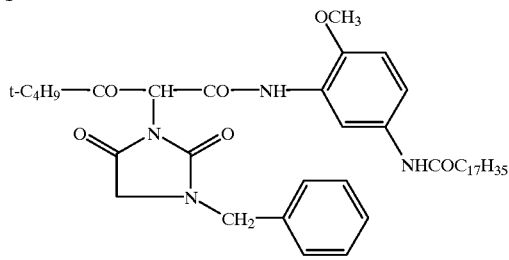

GB-2

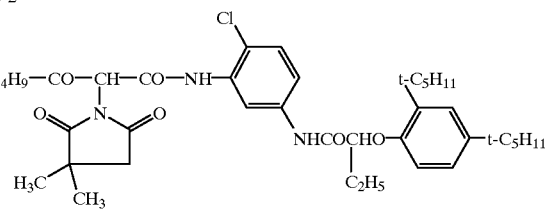

SC

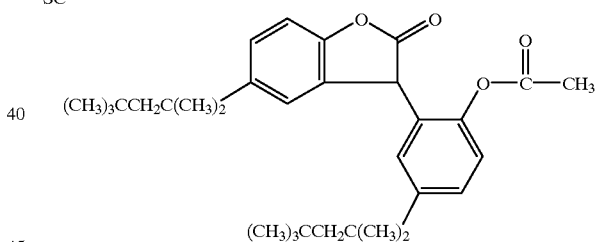

WK

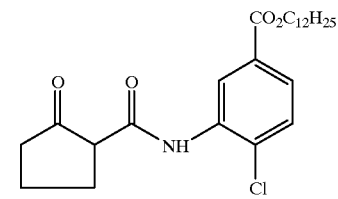

PP-1

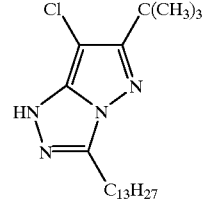

ST-1

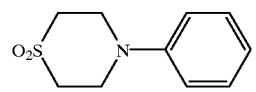

ST-2

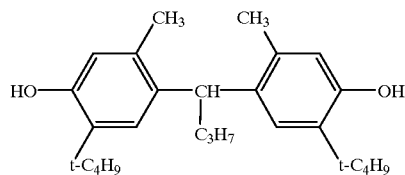

UV

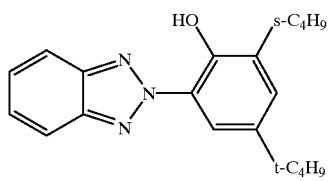

BG-1

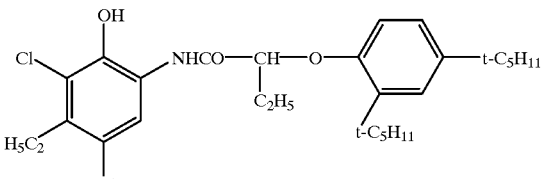

HM

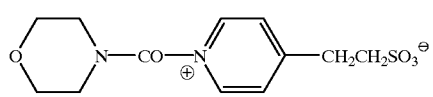

The colour photographic recording material is exposed through a step wedge. During exposure, additional filters are placed in beam path of the exposure unit such that the wedge appears neutral at an optical density of D=0.6.

The material was processed under the following conditions:

| Step | Time | Temperature |
|---|---|---|
| Development | 27 sec | 39° C. |
| Bleach/fixing | 27 sec | 35° C. |
| Stabilisation | 54 sec | 33° C. |

The colour developer used in one instance was the ready-to-use developer prepared from concentrate 1-1 and in the other instance that prepared from concentrate 1-2.

Bleach/Fixing Bath

| Ammonium thiosulfate solution, 58 wt. % | 110 ml |
|---|---|
| Ammonia, 25 wt. % | 2.7 ml |
| Sodium disulfite | 16.2 g |
| Ammonium/iron EDTA, 48 wt. % | 101 ml |
| Acetic acid, 85 wt. % | 7.7 ml | make up with water to 1000 ml; adjust pH value to 5.85 with ammonia or phosphoric acid.

Stabilising Bath

| Water | 900 ml |
|---|---|
| Sodium disulfite | 2 g |
| Hydroxyethanediphosphonic acid disodium salt | 4 g |
| Sodium benzoate | 0.5 g |
| make up with water to 1000 ml. | |

Drying

A comparison of materials processed in the two developers revealed no significant sensitometric difference.

What is claimed is:

1. One-part, multi-phase color developer concentrate which comprises an aqueous phase and an organic phase, wherein the organic phase is constituted by one or more partially water-miscible solvents and the concentrate contains at least one compound of the formulae (I), (II) or (III) as antioxidant:

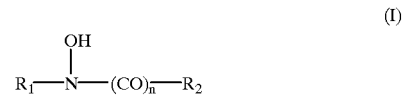

(I)

in which $R_1$ means alkyl, $R_2$ means alkyl or aryl and n means 0 or 1 and at least one of the residues $R_1$ and $R_2$ contains at least one —OH, —COOH or —$SO_3$H group;

(II)

in which $R_3$ means an alkyl or acyl group;

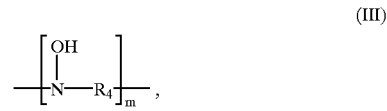

(III)

in which $R_4$ means an alkylene group optionally interrupted by O atoms and m means a number of at least 2, wherein the alkyl, alkylene and aryl groups may be further substituted.

2. The color developer concentrate according to claim 1, wherein said antioxidant is in a quantity of 0.1 to 5 mol/l or, as far as oligomeric and polymeric compounds are concerned, in a quantity of from 10 to 500 g/l of concentrate.

3. The color developer concentrate according to claim 1, wherein the color developer substance is 4-N-ethyl-4-N-(2-methylsulfonylaminoethyl)-2-methyl-p-phenylenediamine.

4. The color developer concentrate according to claim 1, wherein the antioxidant is selected from the group consisting of

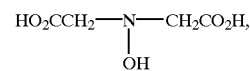

-continued

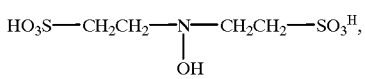

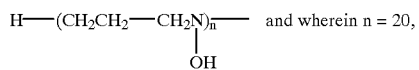

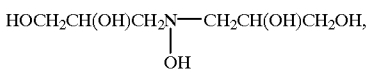

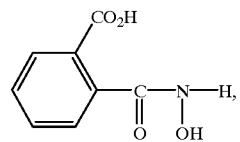

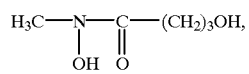

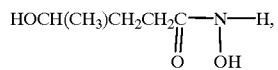

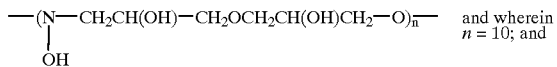 and wherein $n = 10$; and

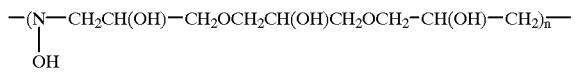 and wherein $n = 5$.

5. The color developer concentrate according to claim 4, wherein the antioxident is

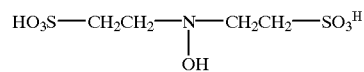

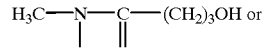 or

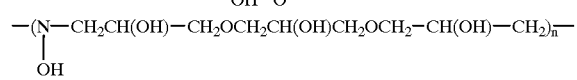

and wherein $n = 5$.

6. The color developer concentrate according to claim 5, wherein said solvent is carboxylic acid amide and urea derivative; aliphatic alcohol; cyclic alcohol; aliphatic polyalcohol; cyclic polyalcohol; aliphatic ketone; cyclic ketone; aliphatic carboxylic acid ester or orthoester; cyclic carboxylic acid ester or orthoester; aliphatic phosphonic acid ester; cyclic phosphonic acid ester; aliphatic oxoalcohol; cyclic oxoalcohol; aliphatic aldehyde; cyclic aldehyde; aliphatic oxime; cyclic oxime; aliphatic amine; cyclic amine; aliphatic polyamine; cyclic polyamine; aliphatic hydroxyamine or cyclic hydroxyamine.

7. The color developer concentrate according to claim 5, wherein the solvent is caprolactam, polyglycol, glycols, dimethylacetamide or triethanolamine.

8. Process for developing a color photographic silver halide material, at least 95 mol % of the silver halides of which consist of AgCl, a color developer produced from the color developer concentrate according to claim 1 is used.

* * * * *